United States Patent
Tanaka et al.

(10) Patent No.: US 7,229,971 B2
(45) Date of Patent: Jun. 12, 2007

(54) REGULATION OF BIODEGRADABILITY OF COMPOSITE BIOMATERIALS

(75) Inventors: Junzo Tanaka, Ibaraki (JP); Masanori Kikuchi, Ibaraki (JP); Noriichi Ito, Osaka (JP); Yoshinobu Mandai, Osaka (JP); Hiroko Matsumoto, Tokyo (JP); Yoshihisa Koyama, Kanagawa (JP); Kazuo Takakuda, Tokyo (JP)

(73) Assignees: Japan Science and Technology Agency, Saitama (JP); National Institute for Materials Science, Ibaraki (JP); Nitta Gelatin Inc., Osaka (JP)

( * ) Notice: Subject to any disclaimer, the term of this patent is extended or adjusted under 35 U.S.C. 154(b) by 0 days.

(21) Appl. No.: 10/937,732

(22) Filed: Sep. 10, 2004

(65) Prior Publication Data

US 2005/0042252 A1     Feb. 24, 2005

Related U.S. Application Data

(63) Continuation-in-part of application No. PCT/JP02/08335, filed on Aug. 19, 2002, and a continuation-in-part of application No. PCT/JP02/12971, filed on Dec. 11, 2002.

(30) Foreign Application Priority Data

Mar. 11, 2002   (JP)   ............... 2002-065831
May 14, 2002   (JP)   ............... 2002-138989

(51) Int. Cl.
 *A61K 38/39*  (2006.01)
(52) U.S. Cl. .................. 514/21; 424/422; 530/356
(58) Field of Classification Search .............. None
See application file for complete search history.

(56) References Cited

U.S. PATENT DOCUMENTS 4,623,553 A  * 11/1986 Ries et al. ............... 427/2.27
5,955,438 A   9/1999 Pitaru et al.
6,887,272 B2 * 5/2005 Shinomiya et al. ...... 623/17.11

FOREIGN PATENT DOCUMENTS

| | | |
|---|---|---|
| JP | 8-276003 | 10/1996 |
| JP | 10-127753 | 5/1998 |
| JP | 11-199209 | 7/1999 |
| JP | 2000-5298 | 1/2000 |
| JP | 2001-191446 | 7/2001 |
| JP | 2001-198208 | 7/2001 |
| JP | 2002-143291 | 5/2002 |
| JP | 2002-248119 | 9/2002 |

OTHER PUBLICATIONS

John et al., "A trial to prepare biodegradable collagen-hydroxyapatite composites for bone repair", J. Biomater. Sci. Polymer Edn. 12(6): 689-705 (2001).*

Glutaraldehyde Chronic Toxicity Summary sheet (1 page), www.oehha.ca.gov/air/chronic_rels/pdf/111308.pdf. (downloaded Mar. 23, 2006).*

Masanori Kikuchi et al.; Journal of Oromaxillofacial Biomechanics; vol. 7, No. 1, pp. 145-146, 2001. Cited in the PCT search reports, abstract only.

English translation of International Preliminary Examination Report for PCT/JP02/08335 with Form PCT/IB/338.

English translation of International Preliminary Examination Report for PCT/JP02/12971 with Form PCT/IB/338.

* cited by examiner

*Primary Examiner*—Robert A. Wax
*Assistant Examiner*—Anand Desai
(74) *Attorney, Agent, or Firm*—Westerman, Hattori, Daniels & Adrian, LLP.

(57) ABSTRACT

This invention relates to a method for regulating the biodegradability of composite biomaterials comprising calcium salt (particularly hydroxyapatite) and collagen, improved composite biomaterials obtained via such method, and a method for increasing bone mass with the use of such composite biomaterials.

16 Claims, 8 Drawing Sheets

OVX Normal (Left: Control)

Fig 6

OVX Nomral (Right: HAp/Col)

REGULATION OF BIODEGRADABILITY OF COMPOSITE BIOMATERIALS

CROSS-REFERENCE TO RELATED APPLICATIONS

This application is a continuation-in-part of PCT/JP02/08335, filed Aug. 19, 2002, and PCT/JP02/12971, filed Dec. 11, 2002.

TECHNICAL FIELD

The present invention relates to a method for regulating the biodegradability of composite biomaterials comprising calcium salt (particularly hydroxyapatite) and collagen, improved composite biomaterials obtained via such method, and a method for increasing bone mass with the use of such composite biomaterials.

BACKGROUND ART

In the field of orthopedics, bone defects used to be often reconstructed by transplanting a patient's own tissues in the past. Use of a patient's own tissues, however, imposes a heavy burden on a patient, and supply source are limited. Accordingly, it is necessary to reconstruct bone defects with artificial implants. Such artificial implants are required to have bioadaptability and bone conductivity in addition to mechanical properties similar to those of natural bones. That is, artificial implants need to be gradually absorbed after implantation in the body, involved into the bone regeneration cycle, and then substituted for the bones of the patient.

Bones of vertebrates are originally composed of an inorganic substance (hydroxyapatite (HAp)) and an organic substance (mainly collagen). They form a specific nanocomposite structure in natural bones characterized in that the c-axis of HAp is oriented along collagen fibers (self-organization), and this structure imparts bone-specific mechanical properties. Specifically, a simple combination of HAp and collagen cannot provide structures or properties similar to those of natural bones.

A variety of studies have been conducted in order to develop composite biomaterials that are more similar to natural bones with the use of HAp and collagen. For example, Mehlisch et al. synthesized a mixture of HAp particles with collagen (Mehlisch, A. S. et al., Oral Surg Oral Med Oral Pathol, 70 (6), 1990, pp. 685–692), and Miyamoto et al. prepared collagen that had been reinforced with a HAp cement and evaluated its bioaffinity (Y. Miyamoto et al., Biomaterials, 19, 1998, pp. 707–715). Also, TenHuisen et al. employed calcium hydrogen phosphate as a precursor of HAp to allow a HAp crystal to grow on a collagen (Col) fiber to produce an HAp/Col nanocomposite (K. S. TenHuisen et al., J. Biomed Mater Res, 29 (7), 1995, pp. 803–810). None of these techniques, however, were able to reproduce nanocomposite structures similar to those of natural bones.

The present inventors had successfully synthesized an HAp/Col composite having a nanocomposite structure similar to that of natural bones under biomimetic conditions (which is similar to the in vivo environment where osteogenesis takes place) with the utilization of HAp and Col self-organization (e.g., JP Patent Publication (Kokai) Nos. 7-101708 A (1995), 11-199209 A (1999), and 2000-5298 A). This composite was found to have excellent bioaffinity, to be absorbed by osteoclasts, and to accelerate osteogenesis. This composite was, however, disadvantageously absorbed and degraded immediately after implantation and thus was less useful for artificial bone materials and the like.

Osteoporosis refers to a clinical condition resulting from bone loss caused by an amount of bone absorption exceeding the amount of bone formation during the process of bone remodeling in which old bones are replaced with new bones. In the past, a major treatment for osteoporosis used to be the use of medicines for internal application. This was aimed at inhibiting bone absorption and accelerating bone formation. At present, the most common treatment is the combined use of a hormone preparation (estrogen), a calcium preparation, vitamin D, a derivative thereof, or the like to improve the systemic bone metabolism with. In this treatment, however, the dose of an agent is limited in view of side effects. Accordingly, significant effects cannot be attained within a short period of time. Such agent has the effect of preventing the bone trabeculae that have been thinned due to osteoporosis from being further absorbed, and also has the effect of thickening the thinned bone trabeculae to some extent. However, it cannot newly form bone where bone trabeculae have been absorbed and lost.

Bone morphogenic proteins (BMP), which are currently in the experimental phase, are said to be capable of actively forming bone. They, however, have problems in that they are expensive, continuous effects cannot be attained therefrom due to the absence of an ideal carrier, and frequent administration thereof is necessary.

A treatment for osteoporosis in which materials for topical application, such as biological implants, are used has not substantially been carried out in the past. In fact, many of the existing bone filler materials are non-absorbable by the body, and thus effective bone formation cannot be expected. For example, a commercially available bone filler material, i.e., a sintered apatite, does not have bioabsorbability. If the granules thereof are used to fill in defective bones, therefore, they are considered to permanently remain in the body without being replaced by bone.

If a material for biological implantation having an excellent effect of bone mass increase were to be developed, such material would be very useful as a material for topically increasing bone mass at a desired site, such as a femur at risk of fracture of an osteoporosis patient who cannot be systemically treated with the use of an existing agent.

DISCLOSURE OF THE INVENTION

An object of the present invention is to provide composite biomaterials having structures similar to those of natural bones and comprising calcium salt (particularly hydroxyapatite) and collagen that are suitable for practical use by regulating the biodegradation rate while maintaining mechanical strength.

The present inventors have conducted concentrated studies in order to attain the above object. As a result, they have found that crosslinking to collagen fibers constituting the composite enabled regulation of mechanical strength and biodegradation rate. Further, they have also found that the bone density in the vicinity of the implantation site was obviously improved via implantation of this composite into the bone of an animal model of osteoporosis. This has led to the completion of the present invention.

Specifically, the present invention relates to a method for regulating the biodegradation rate of composite biomaterials comprising calcium salt and collagen by introducing crosslinking to collagen in the aforementioned biomaterials. In this method, calcium salt is preferably hydroxyapatite, and composite biomaterials preferably have self-organized composite fibers having a microstructure in which the c-axis of the hydroxyapatite is oriented along the collagen fibers and have a dense and porous structure comprising such fibers.

In the method of the present invention, the crosslinking is preferably introduced in at least 1% of reactive functional groups in collagen.

The crosslinking is preferably introduced by, for example, a reaction utilizing glutaraldehyde, and 10 µmol to 10 mmol of the glutaraldehyde is preferably used per g of collagen in composite biomaterials.

The present invention also relates to composite biomaterials comprising hydroxyapatite and collagen, wherein crosslinking is introduced to collagen.

The crosslinking is preferably introduced by, for example, utilizing 10 µmol to 10 mmol of glutaraldehyde per g of collagen, and the crosslinking is particularly preferably introduced in at least 5% of reactive $\epsilon$-amino groups in collagen.

The composite biomaterials preferably have microstructures similar to those of natural bones, in which the c-axis of hydroxyapatite is oriented along the collagen fibers.

Further, the present invention relates to a method for increasing bone mass of a subject with the use of the composite biomaterials of the present invention. This method can be utilized in, for example, the treatment of osteoporosis.

Hereafter, the present invention is described in detail.

1. Composite Biomaterials of the Present Invention

The composite biomaterials of the present invention comprise calcium salt (particularly hydroxyapatite) and collagen, and they have mechanical strength and biodegradation rates suitable for their applications via introduction of crosslinking in collagen.

Calcium salt contained in the composite biomaterials of the present invention is preferably calcium phosphate or calcium carbonate, with hydroxyapatite being the most preferable. In the composite biomaterials comprising hydroxyapatite and collagen, hydroxyapatite and collagen are preferably oriented in a self-organized manner to form composites similar to natural bones. The term "self-organized" generally refers to the "formation of a specific structure characterized by an assembly of homologous or heterologous atoms, molecules, fine particles, or the like through non-covalent interaction" (Seikagaku Jiten (Dictionary of Biochemistry), Tokyo Kagaku Dozin Co., Ltd.). In the present invention, this term particularly refers to a structure characterized by the same orientation of calcium phosphate having an apatite structure (hydroxyapatite (HAp)) along collagen fibers as natural bones, in which the c-axis of HAp is oriented along collagen fibers.

Hydroxyapatite is generally denoted by the chemical formula $Ca_5(PO_4)_3OH$, and it includes a group of compounds referred to as calcium phosphate, such as $CaHPO_4$, $Ca_3(PO_4)_2$, $Ca_4O(PO_4)_2$, $Ca_{10}(PO_4)_6(OH)_2$, $CaP_4O_{11}$, $Ca(PO_3)_2$, $Ca_2P_2O_7$, or $Ca(H_2PO_4)_2 \cdot H_2O$, as evidenced by the nonstoichiometric properties of its reaction. Also, hydroxyapatite is basically composed of a compound represented by the formula $Ca_5(PO_4)_3OH$ or $Ca_{10}(PO_4)_6(OH)_2$, and a part of the Ca component may be substituted with at least one member selected from Sr, Ba, Mg, Fe, Al, Y, La, Na, K, H, and the like. A part of the ($PO_4$) component may be substituted with at least one member selected from $VO_4$, $BO_3$, $SO_4$, $CO_3$, $SiO_4$, and the like. A part of the (OH) component may be substituted with at least one member selected from F, Cl, O, $CO_3$, and the like. Some of these components may be deficient. In general, some of the apatite $PO_4$ and OH components in natural bones are substituted with $CO_3$. Accordingly, inclusion of $CO_3$ from the atmosphere and partial substitution with each component (about 0% to 10% by mass) may occur during the production of the composite materials of the present invention.

Hydroxyapatite is generally microcrystalline, noncrystalline, or crystalline. Alternatively, it may exist in the form of an isomorphic solid solution, substitutional solid solution, or interstitial solid solution. It may comprise a nonstoichiometric deficiency. The atomic ratio of calcium/phosphorus (Ca/P) in this hydroxyapatite is preferably in the range between 1.3 and 1.8. In particular, the range between 1.5 and 1.7 is more preferable. When the atomic ratio is in the range between 1.3 and 1.8, the composition and the crystal structure of apatite in the product (a calcium phosphate compound) can be similar to those in bones of vertebrates. This improves biocompatibility and bioabsorbability.

At present, about 20 different collagen molecular species are known to be present in a wide variety of animal tissues ranging from mammalians to fish. These are generically denoted as "collagens." The species, the location of tissue, the age, and other factors regarding the animal that is a starting material for the collagen used in the present invention are not particularly limited, and any type of collagen can be used. In general, collagens obtained from skin, bones, cartilage, tendons, organs, or the like of mammalians (such as cow, pig, horse, rabbit, or mouse) and birds (such as chicken) are used. Also, collagen-like proteins obtained from skin, bones, cartilage, fins, scales, organs, or the like of fish (such as cod, left-eyed flounder, right-eyed flounder, salmon, trout, tuna, mackerel, sea bream, sardine, or shark) may be used as starting materials. Alternatively, recombinant collagen may be used instead of those extracted from animal tissues.

Among the molecular species of collagens, the quantity of type I collagens is the largest, and they have been well studied. In general, when simple reference is made to "collagen," it often indicates type I collagen. The molecular species of the collagen used in the present invention is not particularly limited, and type I collagen is preferably a main component. Collagen may be prepared by adequately subjecting an amino acid residue of the collagen protein to chemical modification such as acetylation, succination, maleylation, phthalation, benzoylation, esterification, amidation, or guanidination.

Collagen may be prepared by extraction from the aforementioned starting material (excluding the gene recombination technique) by a neutral buffer or dilute acid such as hydrochloric acid, acetic acid, or citric acid. Collagen extracted by the neutral buffer is referred to as neutral salt-soluble collagen, and that extracted by the dilute acid is referred to as acid-soluble collagen. However, the amount of collagen extracted is small in both cases, and a majority thereof remains as insoluble collagen. The enzyme solubilization method and the alkali solubilization method are known as methods for solubilizing such insoluble collagen. Collagen obtained by the enzyme solubilization method is referred to as enzyme-solubilized collagen, and that obtained by the alkali solubilization method is referred to as alkali-solubilized collagen. Both can be solubilized as molecular collagens with yields of substantially 100%.

The method for preparing collagen used in the present invention (extraction type) is not particularly limited. If the molecular weight of solubilized collagen is large, however, the strength of a composite becomes insufficient because of steric hindrance. Accordingly, the use of monomeric (monomolecular) collagen is preferable. In enzyme-solubilized collagen and alkali-solubilized collagen, the monomeric collagen content is high, and non-helical regions (telopeptides) having a majority of collagen antigenicity are selectively degraded and removed during the step of production. Thus, they are particularly adequate for the organic/inorganic composite biomaterials of the present invention. If these non-helical regions are degraded and removed from collagen, the resulting form of collagen is referred to as "atelocollagen."

The isoionic point of enzyme-solubilized collagen is different from that of alkali-solubilized collagen. The isoionic point is the pH level where both positive and negative charges, which are derived from a dissociable group inherent to a protein molecule, repel each other. In the case of collagen, when the pH level approaches the region of the isoionic point, solubilized collagen is known to become fibrous. In general, the isoionic point of the enzyme-solubilized collagen is between pH 8 and 9, and that of the alkali-solubilized collagen is between pH 4 and 5. In the present invention, it is preferable to use the enzyme-solubilized collagen in a reaction vessel maintained at conditions between pH 7 and 11, where the fiberization and self-organization of collagen are likely to occur. Examples of enzymes for solubilization include pepsin, trypsin, chymotrypsin, papain, and pronase. Pepsin and pronase are preferably used from the viewpoint of easy handleability after the enzyme reaction.

2. Method for Producing Composites Comprising Hydroxyapatite and Collagen

A method for producing a composite comprising hydroxyapatite and collagen is described as a preferable example of composites comprising calcium salt and collagen that are matrices for the composite biomaterials of the present invention.

Composites comprising hydroxyapatite and collagen can be produced in accordance with, for example, the method of Kikuchi et al. (M. Kikuchi et al, J., Biomater., 22 (13), 2001, pp. 1705–1711; S. Itoh et al., J. Biomed Mater Res, 2001, pp. 445–453). Such composites are produced from at least three components, i.e., collagen, phosphate, and calcium salt. In the present invention, the phosphate includes phosphoric acid, and the calcium salt includes calcium hydroxide, although they are not technically defined as "salts."

Examples of phosphagens for an aqueous phosphate solution used in the present invention include disodium hydrogen-phosphate, sodium dihydrogen phosphate, dipotassium hydrogen phosphate, potassium dihydrogen phosphate, and phosphoric acid. The aqueous phosphate solution dissolves the collagen, and it is subjected to reactions.

Examples of calcium sources for an aqueous calcium salt solution used in the present invention include calcium carbonate, calcium acetate, and calcium hydroxide. This aqueous calcium salt solution may be a suspension as long as it is homogenous. For example, calcium carbonate is burned and then pulverized using a mortar or the like to prepare calcium hydroxide, and water is added thereto to obtain a suspension of calcium hydroxide. The thus obtained suspension can be preferably used for the present invention.

In the method for producing the composites, the aqueous calcium salt solution and the aqueous phosphate solution containing collagen are simultaneously added dropwise to the reaction vessel. The term "simultaneous" is not limited to addition at the precisely same time. It also includes the form of addition in which a small amount (approximately 0.01 to 5 ml) of each solutions is separately added in alternate shifts. These solutions may be continually or intermittently added as long as they are simultaneously added.

An adequate amount of pure water is previously placed in the reaction vessel. The amount of pure water is not particularly limited. Preferably, it is substantially the same as the amount of the aqueous calcium salt solution to be used.

In the method for production of the present invention, it is important to maintain the calcium ion concentration at 3.75 mM or lower and the phosphate ion concentration at 2.25 mM or lower in the reaction vessel. This is because the preferable self-organization of the composite is impeded if the calcium ion or phosphate ion concentration exceeds the upper limit of the aforementioned range. This impedance is considered to be caused by spontaneous nucleus formation that occurs when the concentrations of ions in the reaction vessel exceed the concentrations thereof in body fluids. More preferably, the calcium ion concentration is maintained at 2.5 mM or lower, and the phosphate ion concentration is maintained at 1.5 mM or lower, so that a composite having an average fiber length of 1 mm or longer can be obtained.

In the aforementioned production method, the ratio of the weight of hydroxyapatite to that of collagen generated in the reaction vessel is preferably between 3:2 and 9:1, and more preferably between 70:30 and 85:15. Specifically, it is important for self-organization that the ratio of the weight of hydroxyapatite to that of collagen when an ideal reaction takes place be more similar to the ratio in the composition of natural bone (75:25).

The ratio of the amount of an aqueous phosphoric acid solution containing collagen to that of an aqueous calcium salt solution is preferably between 3:1 and 1:3. When a small amount of an aqueous phosphoric acid solution containing collagen is used, the resulting material disadvantageously comprises an excess amount of calcium, which results in reduced strength. In contrast, a small amount of an aqueous calcium salt solution causes calcium deprivation and lowers the Young's modulus, which sometimes results in reduced strength (Japanese Patent Publication (Kokai) No. 11-199209 A (1999)).

In the present invention, the pH level of the reaction solution is preferably between 7 and 11, and the reaction solution is preferably added dropwise so as to keep the pH variation within 1. More preferably, the pH level is between 7 and 9, and the pH variation is within 0.5. Native collagen causes sedimentation at the isoelectric point when the pH is between 7 and 11 to regenerate fibers, and calcium phosphate is likely to cause sedimentation in this pH range. Thus, self-organization of calcium phosphate and collagen is promoted in this pH range. When the pH level exceeds 11, water molecules are hydrated around collagen molecules, and it becomes difficult for water molecules to dissociate in the later step of pressing. This could increase the water content, block the self-organization, and deteriorate the strength of the composite. In contrast, both calcium phosphate and collagen become less likely to sediment if the pH level is below 7. When the pH variation exceeds 1, nucleus formation of calcium phosphate on collagen is inhibited, and self-organization is thereby inhibited (Kikuchi et al., Biomaterials 22, 2000, pp. 1705–1711).

In the aforementioned production method, an adequate pH level is easily maintained with the use of a pH controller. A pH controller comprises a means for measuring pH of the reaction solution and a means for controlling the amounts of both solutions to be added. This pH controller regulates the amounts of both solutions to be added based on the pH levels of the both solutions so as to maintain a certain level (e.g., ±0.3) relative to the pH level that was set as an expected value (e.g., pH 10). An example of a pH controller is that manufactured by Nissin. Reaction is preferably carried out while constantly stirring the both aqueous solutions and the reaction solution in order to maintain the uniform pH level of the reaction solution.

In the aforementioned production method, the temperature of the reaction solution is preferably maintained between 35° C. and 40° C. In this temperature range, composite biomaterials can be formed under conditions similar to those in bodies. The sediment generated from the reaction solution is subjected to filtration and dehydration, followed by pressing. Thus, the composite in which hydroxyapatite is oriented and coupled with collagen in a self-organized manner can be obtained.

3. Introduction of Crosslinking

Crosslinking is introduced into collagen fibers constituting the composites comprising calcium salt (particularly hydroxyapatite) and collagen obtained in the aforementioned manner. Preferably, crosslinking is directly introduced without isolating the composite from a reaction solution. A minor amount of collagen or polysaccharides (1 to 100 mol % relative to the amount of collagen in the composite) may be added in order to increase the points of crosslinking.

Any method, such as chemical crosslinking using a crosslinking agent or condensing agent or physical crosslinking using γ rays, ultraviolet rays, thermal dehydration, an electron beam, or the like, may be employed. Examples of crosslinking agents that can be used include: aldehyde crosslinking agents such as glutaraldehyde or formaldehyde; isocyanate crosslinking agents such as hexamethylene diisocyanate; carbodiimide crosslinking agents such as 1-ethyl-3-(3-dimethylaminopropyl) carbodiimide hydrochloride; polyepoxy crosslinking agents such as ethylene glycol diglycidyl ether; and transglutaminase. The amount of a crosslinking agent used is preferably between about 10 μmol and 10 mmol per g of collagen in the composite.

Crosslinking as mentioned above may involve any portions of collagens. Particularly preferable crosslinking occurs between a carboxyl group and a hydroxyl group, between a carboxyl group and a ε-amino group, or between ε-amino groups. Crosslinking is preferably introduced in at least 1%, and more preferably at least 5%, of reactive functional groups. If crosslinking is insufficient, biodegradation takes place rapidly. Thus, sufficient effects of supplementing bone defects cannot be expected. Attention should be given to the use of a crosslinking agent since the excessive use of a crosslinking agent disadvantageously increases the water content in the composite after introduction of crosslinking between fibers constituting a composite and inhibits particle-particle bonds to decrease the strength of the composite.

Among the aforementioned methods for crosslinking, chemical crosslinking using a crosslinking agent such as glutaraldehyde is particularly preferable from the viewpoint of controllability of the degree of crosslinking and bioaffinity of the resulting composite. A method for crosslinking using glutaraldehyde is hereafter described as a preferable embodiment of the present invention.

The reaction solution of a composite comprising hydroxyapatite and collagen obtained in the section above is allowed to age immediately after or 3 hours after synthesis of the composite. Thereafter, glutaraldehyde is added thereto while vigorously stirring, and the mixture is allowed to react for 10 minutes. After crosslinking, the composite is immediately subjected to filtration and washed three times with pure water. Alternatively, the composite is immersed in a 2% glycine solution at 4° C. overnight after being washed with pure water to remove excessive glutaraldehyde. When glycine is used, the composite is further washed three times with pure water to remove glycine and glutaraldehyde that had reacted with glycine.

The amount of glutaraldehyde to be added is preferably 10 μmol to 10 mmol, and particularly preferably 10 μmol to 1 mmol, per g of collagen in the composite biomaterials. The temperature of the reaction solution is preferably maintained between 0° C. and 40° C.

4. Physical Properties (Mechanical Strength and Biodegradation Rate) Improved by Crosslinking The resulting crosslinked composite biomaterials have enhanced mechanical strength and a slower biodegradation rate than non-crosslinked composite biomaterials. Thus, the crosslinked composite biomaterials can remain longer in the body, which is required for artificial bone materials and the like. More specifically, the present invention provides a method for regulating biodegradation rates of the composite biomaterials while maintaining mechanical strength through the introduction of crosslinking between hydroxyapatite and collagen.

The biodegradation rates can be evaluated by, for example, the remaining capacity of the composite biomaterials after implanting them into the bones of mice, rats, rabbits, or the like. Mechanical strength can be evaluated based on, for example, the three-point bending strength or the Young's modulus determined based thereon.

More specifically, the organic/inorganic composite biomaterials that had been crosslinked with 10 μmol to 10 mmol of glutaraldehyde per g of collagen had enhanced mechanical strength of 15 MPa or more after crosslinking, as opposed to 7 MPa before crosslinking. While non-crosslinked samples were substantially absorbed (90% or more thereof) within 4 weeks in natural bones, approximately 50% or more of the crosslinked composite biomaterials remained in natural bones even 4 weeks later.

5. Applications of Composite Biomaterials

The composite biomaterials obtained in the aforementioned manner can be adequately pressed and utilized as implants such as artificial bone materials. Pressing is preferably carried out in a temperature range between 0° C. and 110° C. and in a pressure range between 10 MPa and 5 GPa. When pressing is carried out in this temperature range, most of water contained in the sediment is rapidly removed. Temperature is preferably between 25° C. and 60° C. where a large amount of water is discharged, with the range between 35° C. and 45° C. being particularly preferable.

It is preferable to conduct pressing with ultrasonication since self-organization can be further promoted by this procedure. An example of an apparatus for applying pressure that can be used for pressing in the present invention is the CIP, manufactured by Kobe Steel, Ltd.

The forms and shapes of the composite biomaterials of the present invention are not particularly limited. Biomaterials can take any desired forms or shapes in accordance with the applications thereof. For example, they can be blocks, pastes, films, particles, or sponges. The composite biomaterials of the present invention have excellent biocompatibility, bone inductivity, or bone conductivity. When the composite biomaterials are used as implants, they may be once immersed in an adequate liquid such as physiological saline before use. The implanted composite biomaterials can be rapidly fused with bone tissues and integrated into the hard tissues of the recipient.

The composite biomaterials of the present invention may comprise the essential components, i.e., calcium salt, phosphate, and collagen, as well as other components within the scope of the present invention. Examples of such components include inorganic salts such as St, Mg, and $CO_3$, organic substances such as citric acid and phospholipids, bone morphogenetic proteins, and agents such as anti-cancer agents.

The composite biomaterials of the present invention have strength and compositions similar to those of natural bones. Also, the composite biomaterials of the present invention have effects of sustaining drug release, bone inductivity, and bone conductivity due to the biosolubility of both constituents, i.e., collagen and calcium phosphate. Further, the composite biomaterials of the present invention have adequate mechanical strength and retentivity in organisms (adequate biodegradation rate), which are attained by crosslinking.

The composite biomaterials of the present invention can accelerate the bone metabolic turnover and bone mass increase. When the composite biomaterials are used for increasing bone mass, they can take any desired forms and shapes in accordance with the implantation sites or applications. For example, they can be blocks, pastes, films, or particles. The biodegradation rate and the rate of replacement with bone tissues of the composite biomaterials can be regulated by suitably altering the shapes or sizes thereof.

The composite biomaterials can further comprise other components without damaging the effect of bone mass increase. Examples of such components include inorganic salts such as Sr, Mg, and $CO_3$, organic substances such as citric acid and phospholipids, bone morphogenetic proteins such as BMP-2, BMP-6, and BMP-7, and growth factors such as bFGF, aFGF, VEGF, and TGFβ.

The effect of bone mass increase attained by the composite biomaterials of the present invention can be utilized in topical treatment for osteoporosis (including primary and secondary osteoporosis), osteomalacia, osteoarthritis of spine, chronic rheumatism, malignant tumor, and a decrease in bone mineral content resulting from external injuries and the like. This effect is particularly suitable as a topical therapeutic material for osteoporosis. The composite biomaterials of the present invention can topically increase bone mass at a desired site, such as a femur at risk of fracture of an osteoporosis patient who cannot be systemically treated by the application of an existing therapeutic material for osteoporosis.

Bone marrow, liver, and other tissues can be reconstructed by conducting tissue culture using the composite biomaterials of the present invention containing highly bioactive cytokines as a scaffold in a biomimetic environment applying dynamics or electricity or in vivo. For example, when the composite materials of the present invention containing anti-cancer agents are used for reconstructing bones resected due to osteogenic sarcoma, carcinoma recurrence can be prevented and the generation of hard tissue in the patient can be induced.

Accordingly, the composite biomaterials of the present invention can be extensively utilized in, for example, biological implants for increasing bone mass, particularly a therapeutic material for osteoporosis, artificial bones, artificial joints, cements for tendons and bones, dental implants, percutaneous terminals for catheters, drug carriers for sustained release, chambers for bone marrow induction, and chambers or base materials for tissue reconstruction.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODES FOR CARRYING OUT THE INVENTION

The present invention is hereafter described in more detail with reference to the examples, although the technical scope of the present invention is not limited thereto.

EXAMPLE 1

Preparation of Crosslinked HAp/Col Composites (1) Preparation of HAp/Col Composites HAp/Col composites were prepared in accordance with the method of Kikuchi et al. (M. Kikuchi et al., Biomater., 22 (13), 2001, 1705–1711). At the outset, calcium carbonate (for alkali analysis, Wako Pure Chemical Industries, Ltd.), phosphoric acid (special grade, Wako Pure Chemical Industries, Ltd.), and porcine dermis-derived atelocollagen (Nitta Gelatin Inc.) were prepared as starting materials. Calcium carbonate was burned at 1050° C. and then digested through hydrolysis to prepare single-phase calcium hydroxide. An aqueous solution of phosphoric acid (24 mM, 2 dm$^3$) containing a calcium hydroxide suspension (40 mM, 2 dm$^3$) and collagen (2 g) was introduced into a reaction vessel via a tube pump. The pH level in the reaction vessel was adjusted to 9 using a pH controller, and the temperature was maintained at 40° C. using a warm water bath.

(2) Crosslinking

The reaction solution stand for 3 hours in the state of suspension. A crosslinking agent, glutaraldehyde, was then added thereto while vigorously stirring, and the mixture was allowed to react for 10 minutes. After crosslinking, the composite was immediately filtered and washed three times with pure water. For a control, crosslinking was carried out in the same manner using water-soluble carbodiimide and transglutaminase (condensing agents).

Crosslinking was carried out by varying the amount of glutaraldehyde between 0.0191 and 13.5 mmol, that of water-soluble carbodiimide between 0.0191 and 8.8 mmol, and that of transglutaminase between 19.1 and 1,910 mg, per g of collagen in the composite. With 0.191 mmol/g of glutaraldehyde, all the $\epsilon$-amino groups in collagen molecules can be theoretically crosslinked.

(3) Assay of Property Values

The property values of the resulting crosslinked composites were assayed in the following manner.

(i) Constitution of Composite (Particle Size)

The crosslinked composite dispersed in pure water was observed using a Rapid-VueR transmission electron microscope (Beckman-Colter).

(ii) Three-point Bending Strength

The crosslinked composite was subjected to dehydration by uniaxial pressing at 20 MPa for 24 hours, and the three-point bending strength of the resultant was assayed using the universal testing machine (Autograph AGS-1kN, Shimadzu Corporation). A piece of the crosslinked composite (5×3×20 mm) was subjected to assay at a crosshead speed of 500 μm/min at a span of 15 mm.

(iii) HAp/Col/H$_2$O Ratio

The HAp/Col/H$_2$O ratio of the crosslinked composite that was subjected to pressing was measured using a carbon determinator (RC-412, LECO).

(iv) Swelling Ratio

The composite that was subjected to pressing was immersed in a phosphate buffer (pH of 7.4, 37° C.) for 4 weeks, and the weight thereof was measured to determine the swelling ratio by the following equation.

Swelling ratio (%)=[(Wx−Wo)/Wo]×100

(Wx: initial weight; Wo: weight after immersion)

(v) Degree of Crosslinking

The quantity of $\epsilon$-amino groups was measured by sulfo-SDTB analysis using the crosslinked composite that was subjected to the three-point bending strength test to determine the degree of crosslinking.

(4) Results (i) As a result of observation under the transmission electron microscope, the average fiber length of a glutaraldehyde-crosslinked composite was found to be 44.8 μm, and no macro-orientation was observed between the crosslinked hydroxyapatite and collagen. Thus, crosslinking was found to randomly take place. A nanoscopic structure that was similar to that of natural bones (involving the orientation of single collagen fiber HAp) was substantially maintained. As glutaraldehyde became more concentrated, the color of the composite was changed from dark yellow to brown. This is considered to occur because excessive glutaraldehyde allows crosslinking between self-organized fibers to occur, thereby elongating the fibers of the composite.

Figure 1A:
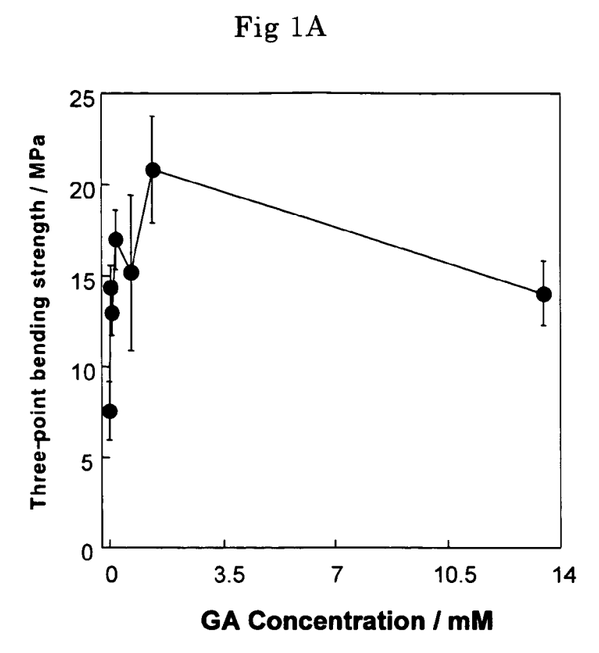
FIG. 1 is a graph showing the correlation between the concentration of a crosslinking agent and the three-point bending strength of the crosslinked composites, wherein: A represents the three-point bending strength of the glutaraldehyde-crosslinked composites; B represents that of the water-soluble carbodiimide-crosslinked composites; and C represents that of the transglutaminase-crosslinked composites.
Figure 1B:
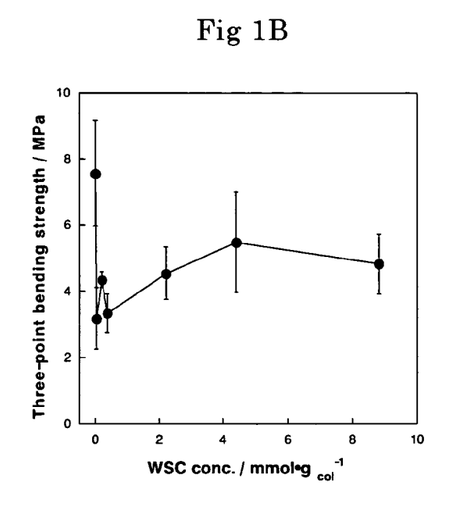
Figure 1C:
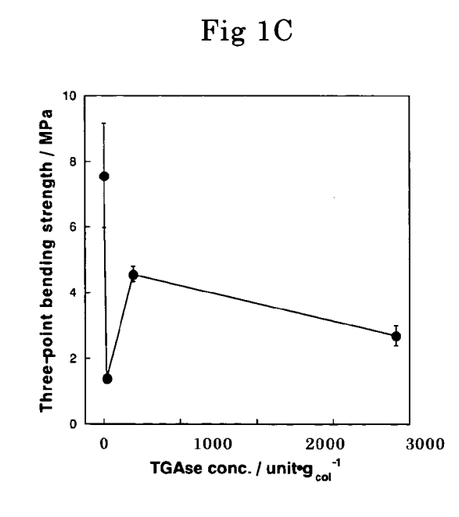

(ii) In the case of a glutaraldehyde-crosslinked composite, the three-point bending strength was enhanced as the glutaraldehyde content increased, and it reached a maximal value at 1.35 mmol/g of collagen (FIG. 1). This indicates that an excess amount of glutaraldehyde crosslinking agent (1.35 mmol/g or more) introduces crosslinking between fibers constituting the composite and increases the water content thereof, which disadvantageously inhibits a particle-particle bond and deteriorates the strength of the composite.

In the case of water-soluble carbodiimide- or transglutaminase-crosslinked composites, the three-point bending strength was not always affected by the concentration of the crosslinking agent.

(iii) The HAp/Col ratio in the glutaraldehyde-crosslinked composite was at a substantially constant level. However, the water content increased as the amount of glutaraldehyde increased for the following reason. Crosslinking that occurs within a self-organized fiber does not affect water retentivity of the composite, although crosslinking that occurs between self-organized fibers improves the water retentivity thereof. In the case of water-soluble carbodiimide or transglutaminase, the collagen and water contents also increased as the concentration of the reaction agent increased, as with the case of glutaraldehyde.

Figure 2A:
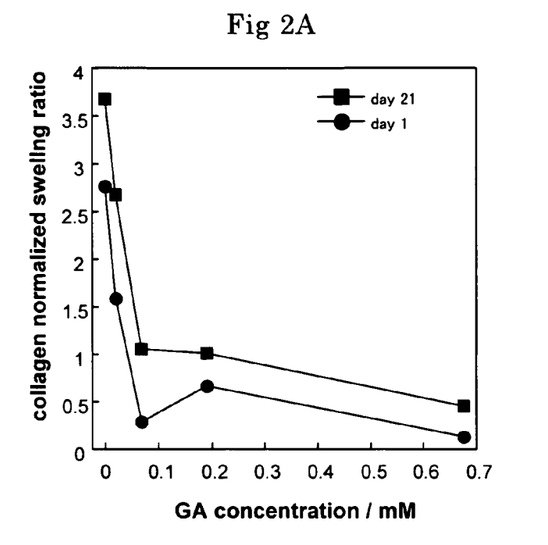
FIG. 2 is a graph showing the correlation between the concentration of a crosslinking agent and the swelling ratio of the crosslinked composites (collagen-normalized), wherein: A represents the swelling ratio of the glutaraldehyde-crosslinked composites; B represents that of the water-soluble carbodiimide-crosslinked composites; and C represents that of the transglutaminase-crosslinked composites.
Figure 2B:
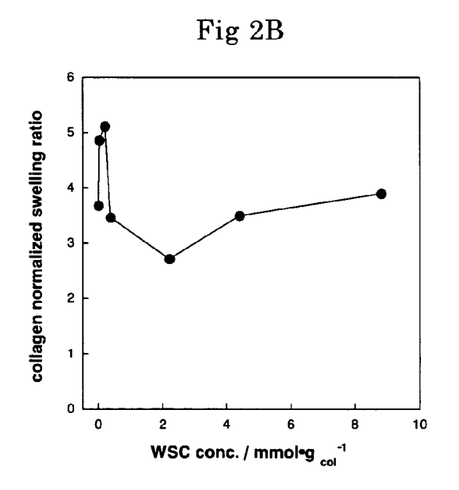
Figure 2C:
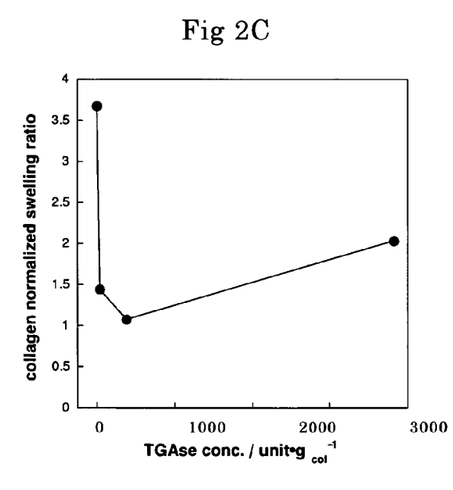

(iv) Since the swelling ratio depends mainly on the amount of collagen, the collagen-normalized swelling ratio that reflected the degree of crosslinking was determined (FIG. 2). As a result, the swelling ratio was found to decrease depending on the concentration of glutaraldehyde, and biodegradability of the composite in body tissues could be regulated by crosslinking.

In contrast, the swelling ratio was not obviously increased in the case of water-soluble carbodiimide or transglutaminase for the following reason. Since water-soluble carbodiimide and transglutaminase are condensing agents, crosslinking results in the preparation of densified composites, thereby inhibiting swelling.

(v) Results of sulfo-SDTB analysis demonstrated that no free $\epsilon$-amino group was detected at a glutaraldehyde content of 1.35 mmol per g of collagen. This concentration was approximately 70 times higher than that of glutaraldehyde required for crosslinking crosslinkable functional groups in collagen.

(5) Results

The mechanical strength of the glutaraldehyde-crosslinked composite was deteriorated when the glutaraldehyde content exceeded 1.35 mmol per g of collagen. Thus, glutaraldehyde was suitably added in an amount of 10 mmol or lower per g of collagen in order to maintain suitable mechanical strength for artificial bone materials. If the biodegradation rate was proportional to the swelling ratio, a higher degree of crosslinking could result in more efficient inhibition of degradation. Nanoscopic structures (involving the orientation of single collagen fiber HAp) similar to those of natural bones were substantially maintained even after crosslinking.

EXAMPLE 2

Figure 3:
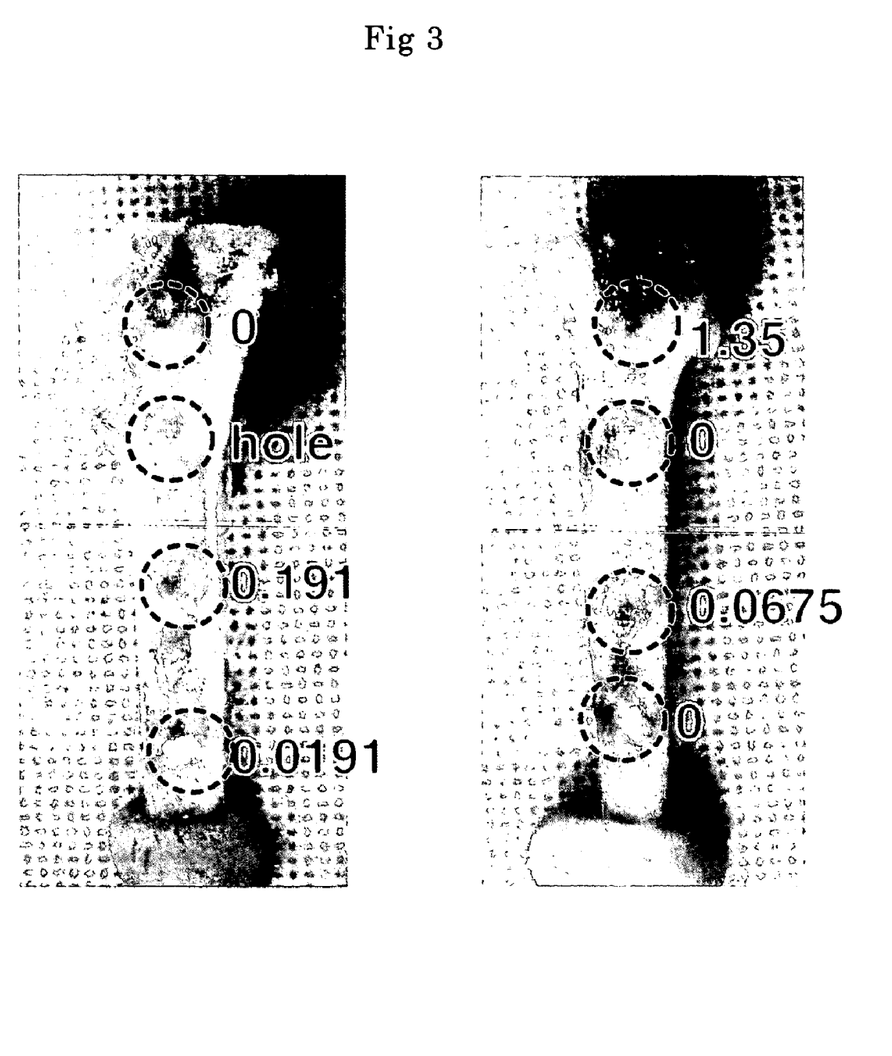
FIG. 3 is a photograph showing the glutaraldehyde-crosslinked composites 2 weeks after implantation in a rabbit tibia, wherein numerical values represent the concentrations of glutaraldehyde ($mmol \cdot g_{col}-1$).

Test for Biodegradability of Crosslinked HAp/Col Composites Using Rabbit (1) Testing Method The biodegradability of the crosslinked HAp/Col composites was inspected by implanting the glutaraldehyde-crosslinked composites with various glutaraldehyde contents obtained in Example 1 (2×2×2 mm) in a rabbit tibia. These crosslinked composites were evaluated by visual inspection (FIG. 3) and by histological examination (hematoxylin-eosin staining) 1, 2, and 4 weeks after implantation.

(2) Results

The results of histological examination demonstrated that no toxic reaction, such as inflammatory reaction, was caused by the glutaraldehyde-crosslinked composites. Bone formation and bone conductivity equivalent to those in the case of non-crosslinked composites were observed in the vicinities of all the crosslinked composites.

The absorption/degradation rate of the crosslinked HAp/Col composites was reduced as the glutaraldehyde content increased. In the case of the composite with high-degree of crosslinking (191 µmol or more), 70% to 80% of the composites still remained in bones even 4 weeks later. Specifically, approximately 50% of the composites crosslinked with 19.1 µmol of glutaraldehyde per g of collagen remained, and approximately 85% or more of the composites crosslinked with 675 µmol of glutaraldehyde per g of collagen remained. Further, only the surfaces of the composites crosslinked with 1.35 mmol of glutaraldehyde per g of collagen were absorbed, and 95% or more of the composites still remained. The proportions of remaining ε-amino groups in each of the crosslinked samples were 80% to 95%, 0% to 10%, and 0%, respectively. In particular, when the composite was crosslinked with 1.35 mmol of glutaraldehyde, an excess amount of glutaraldehyde formed a crosslinking network in the composites and further inhibited absorption of the composites.

(3) Conclusion

Accordingly, composites crosslinked with 19.1 µmol to 1.35 mmol of glutaraldehyde per g of collagen were found to have the mechanical strength and the biodegradation rate required for artificial bone materials. Based on the above results and the results obtained in Example 1, the biodegradation rate required for artificial bone materials could be realized while maintaining mechanical strength, if crosslinking were introduced to at least 1% of reactive ε-amino groups in collagen (preferably at least 5%) in the composite comprising hydroxyapatite and collagen. In such introduction of crosslinking, use of at least approximately 10 µmol to 10 mmol of glutaraldehyde per g of collagen was considered to be sufficient.

EXAMPLE 3

Bone Formation by Implanting Hydroxyapatite/Collagen (HAp/Col) Composite in Rat Model of Osteoporosis 1. Testing Method (1) Preparation of Rat Models of Osteoporosis 5-week-old female SD rats (n=13) were prepared, and they were subjected to ovariectomy (OVX) or sham-operation (Sham) at the age of 6 weeks. All rats were fed with low calcium (Ca) diets (Ca: 0.01%, P: 0.2%; CLEA Japan, Inc.) and distilled water up to the age of 10 weeks to lower bone mineral content. Thus, rat models of osteoporosis were prepared.

(2) Preparation of HAp/Col Composite and Implantation Thereof in Rat Tibia

HAp/Col composites having structures similar to those of natural bones were produced in accordance with the method of Kikuchi et al. (Kikuchi, S. et al., J. Biomater., 22 (13), 2001, 1705–1711; S. Itoh et al., J. Biomed Mater Res., 2001, 445–453). The prepared composites were implanted in 10-week-old rat models of osteoporosis. Holes (diameter: 2 mm) were provided in the external cortical bones of the tibial diaphyses of a rat, an HAp/Col composite having the same diameter was implanted in the right tibia, and the hole on the left tibia was left open as a control.

(3) Culturing after Implantation of HAp/Col Composite

Figure 4:
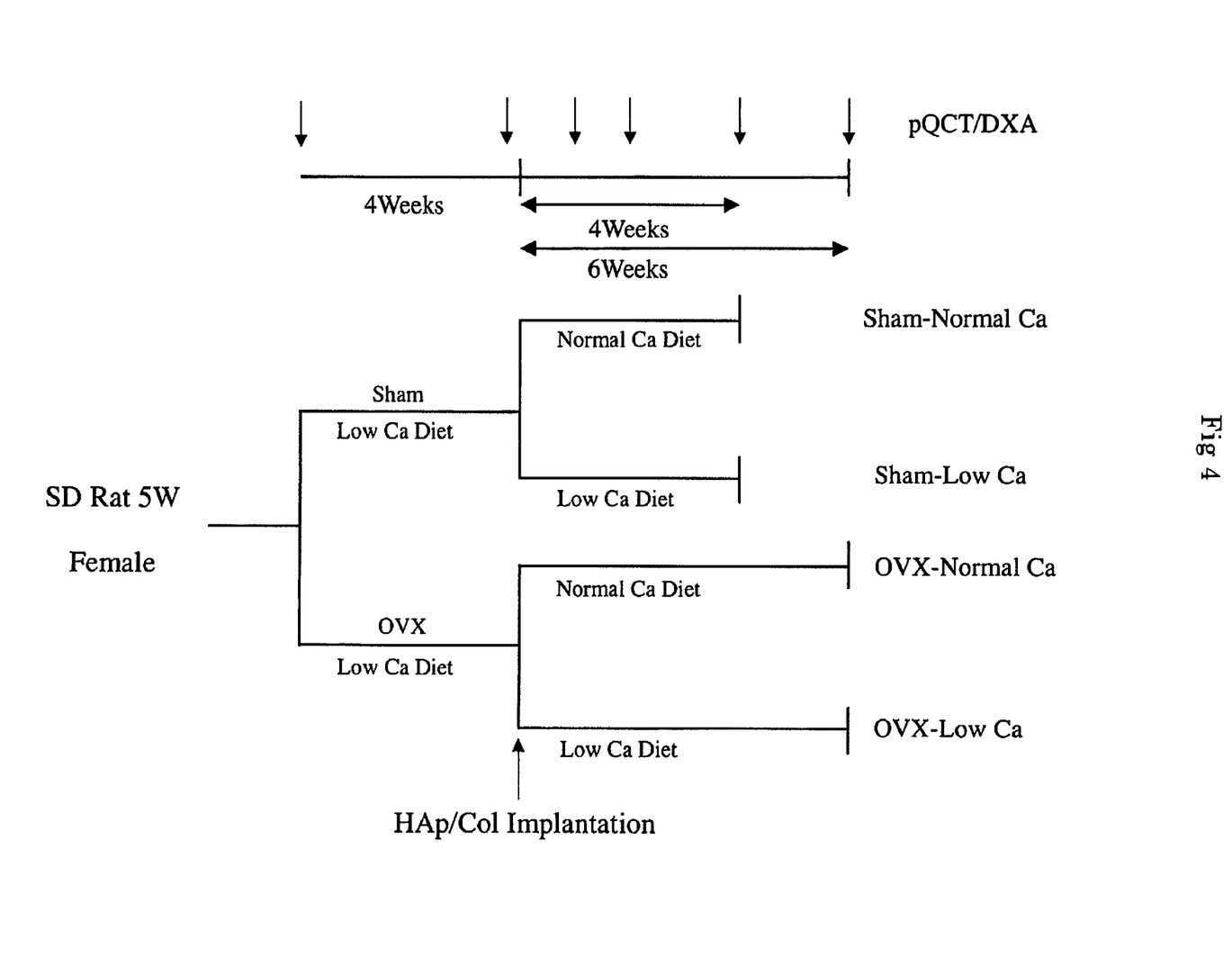
FIG. 4 shows a protocol for the experiment described in Example 3.
Figure 5:
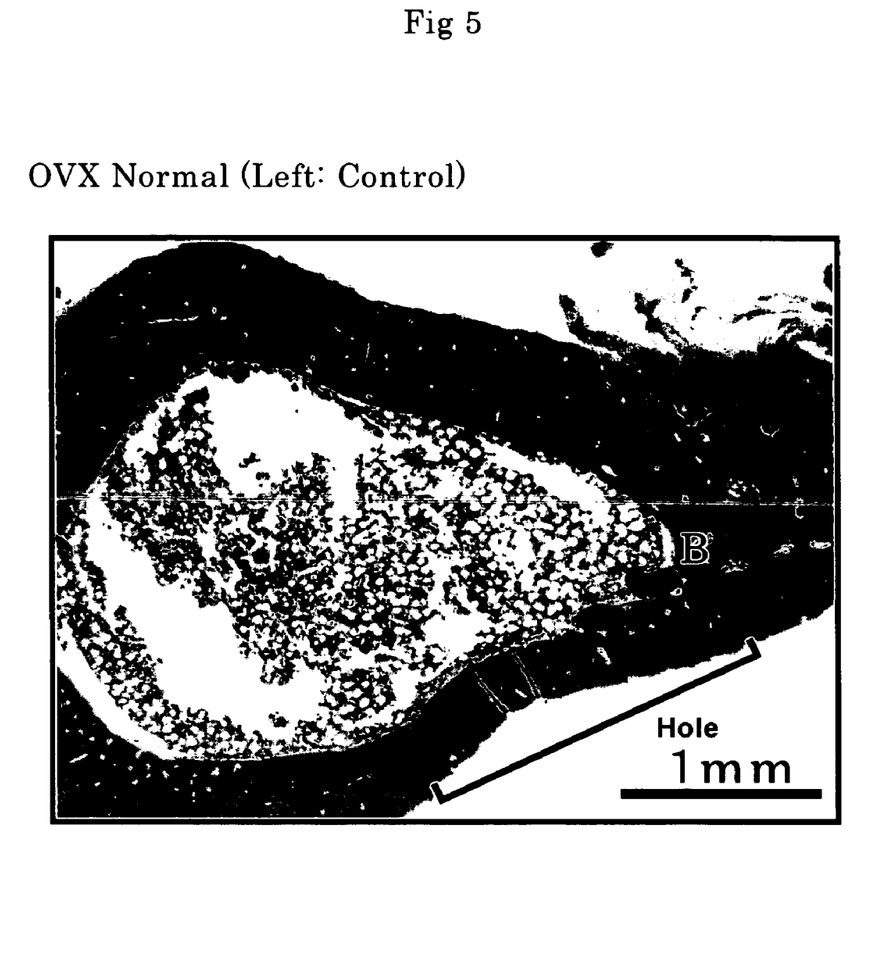
FIG. 5 shows images of HE staining in the control side (a hole only) of the rats of the OVX-Normal Ca group. Six weeks after implantation, although the bone defects of the ovariectomized (OVX) rats had been filled, the cortical bones thereof were thin. (B: newly formed bones).

After implantation, rats were divided into the following 4 groups. A summary of the experimental protocol after the HAp/Col composite implantation is shown in FIG. 4.

The groups were as follows:
 (i) the Sham-Normal Ca group (n=3): Sham-operated (Sham) and fed with a normal Ca diet;
 (ii) the Sham-Low Ca group (n=2): Sham-operated and fed with a low Ca diet;
 (iii) the OVX-Normal Ca group (n=4): ovariectomized (OVX) and fed with a normal Ca diet; and
 (iv) the OVX-Low Ca group (n=4): ovariectomized and fed with a low Ca diet.

General solid feed for laboratory animals (1.11% Ca, 0.83% P, Oriental Yeast Co., Ltd.) was used for a normal Ca diet. In order to avoid individual differences in rats' bone metabolisms caused by body weight differences, the amount of feed to be provided was determined based on the body weight of a given rat (the amount of feeding: 0.05 g/day per g of the body weight, pair-feeding). Rats were allowed to freely ingest water.

(4) Evaluation

The bone density and the morphological changes of the tibia were inspected using pQCT (XCT 960 A, Stratec Medizintechnik GmbH) with the elapse of time.

Rats were sacrificed after a given period (4 or 6 weeks after implantation), and tibiae were excised therefrom. The HAp/Col composite was extracted together with the bone tissue in the vicinity of the implantation site, fixed in formalin, demineralized, and thinly sectioned. The resultant was subjected to hematoxylin-eosin staining (HE staining) for histological observation.

2. Results of Test

Four weeks after implantation of the HAp/Col composites, the cancellous bone density in the tibial epiphyseal area of the OVX-Low Ca group was significantly lower than that of the OVX-Normal Ca group or that of the Sham group ($p<0.001$). While ovariectomized (OVX) animals were already recognized as experimental animal models of osteoporosis, rat models of osteoporosis were also found to be produced via experimental calcium deprivation through OVX and a low calcium diet since lowered bone density can be induced in the OVX-Low Ca group of this experiment.

Figure 6:
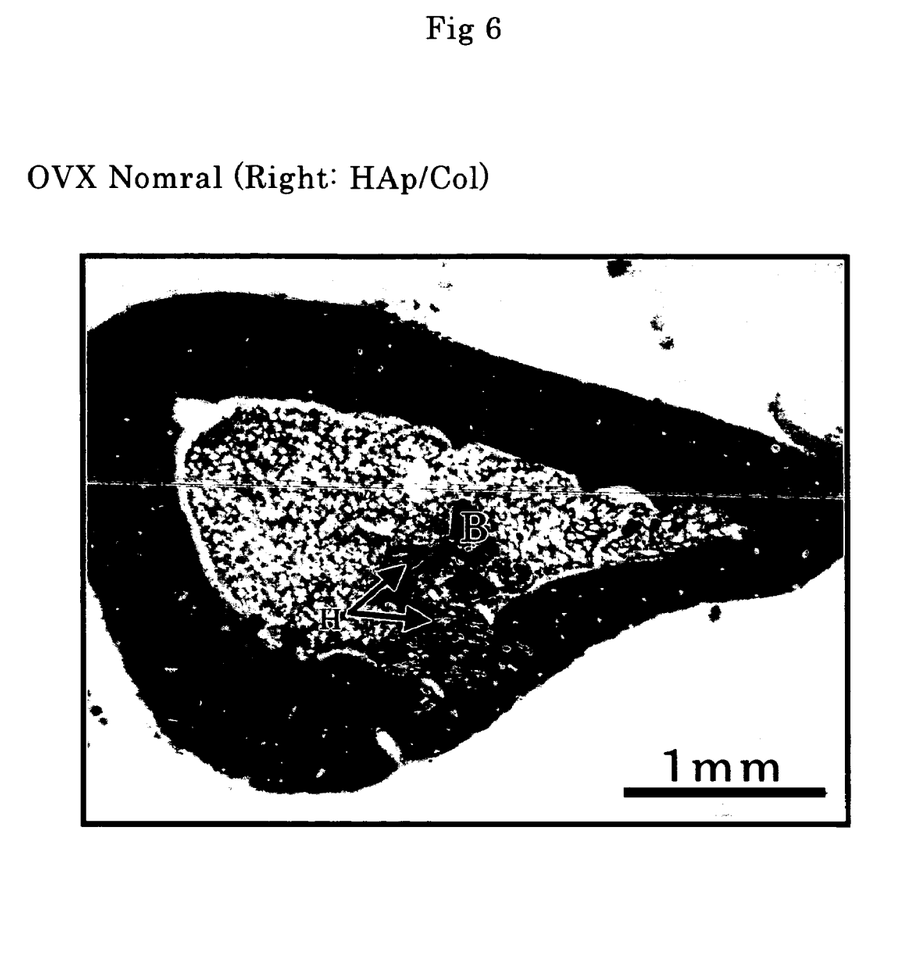
FIG. 6 shows images of HE staining of the tibia of the group of OVX-Normal Ca rats in which HAp/Col had been implanted. A small amount of HAp/Col remained, and newly formed bones began to be generated in the vicinity of the implantation site (B: newly formed bones, H: HAp/Col).

In the case of the OVX-Low Ca group, the HAp/Col composites were immediately absorbed, and HAp/Col was not substantially observed 6 weeks later. In other experimental groups, newly formed bones were found to be generated in the vicinity of the composite that remained in the body, based on the HE-stained image 6 weeks after implantation (FIG. 6). This immediate absorption of the composites observed in the OVX-Low Ca group was considered to result from the increased activity of bone absorption of osteoblasts under estrogen- or calcium-deprived conditions caused by the ovariectomy.

Figure 7:
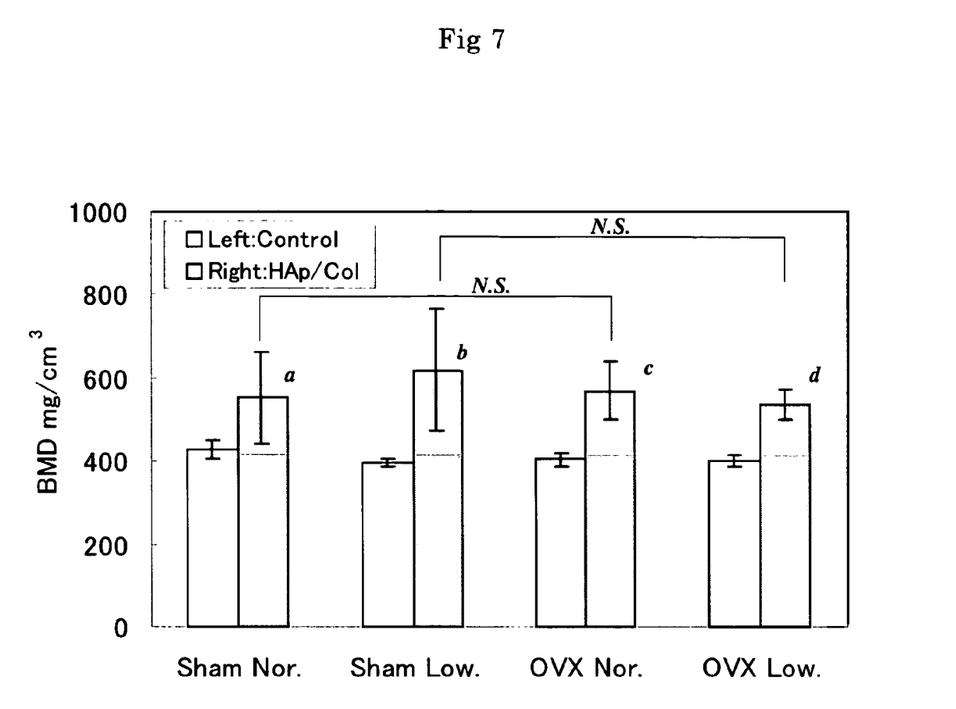
FIG. 7 is a graph showing the cancellous bone density 4 weeks after implantation of HAp/Col, wherein a, b, c, and d indicate that there were significant differences between an implanted site (right tibia) and a control site (left tibia) in all groups ($p<0.01$, by student's t-test).
Figure 8:
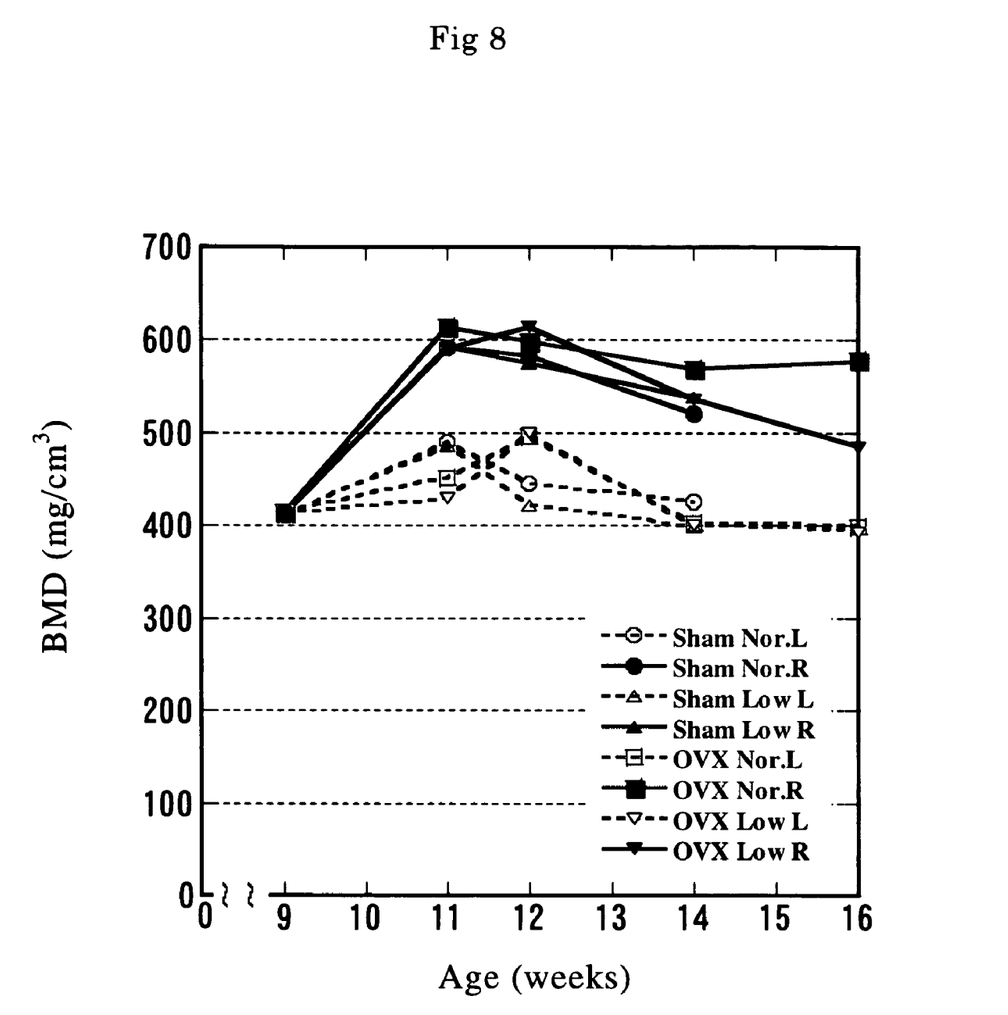
FIG. 8 is a graph showing the cancellous bone density in the implantation site. Significant differences were observed between an implanted site (right tibia) and a control site (left tibia) 1 week after implantation (11-week-old) and thereafter in all groups ($p<0.01$, by student's t-test).

In all the experimental groups, the cancellous bone density at the site where the HAp/Col composites had been implanted became significantly higher than that at the control site (left tibia) (FIG. 7 and FIG. 8). Specifically, increased bone formation via implantation of the HAp/Col composites was observed not only in a normal state (the Sham-Normal Ca group) but also in an extremely calcium-deprived state (the OVX-Low Ca group).

The OVX-Normal Ca group had been fed with a low Ca diet for 4 weeks and then with a normal Ca diet and orally supplied with calcium. The bone density was, however, not improved in the control site. In contrast, the cancellous bone density in the vicinity of the implantation site was enhanced to a level equivalent to that of the normal state (the Sham-Normal Ca group) in the HAp/Col composite-implanted site (right tibia) (FIG. 7).

The cancellous bone density of the OVX-Low Ca group was also enhanced to a level equivalent to that of the normal state (the Sham-Normal Ca group) via implantation of the HAp/Col composite.

Under the present experimental conditions, the cortical bone density was not obviously affected via implantation of the HAp/Col composite. The implanted HAp/Col composite was considered to be reutilized in the formation of new cancellous bone after it had been absorbed by the body. That is, it was deduced that the cancellous bone, which had been first formed, was absorbed and replaced by the cortical bone in acute bone formation, such as in the method of treating bone defects that had been implemented in this experiment.

3. Conclusion

Accordingly, the HAp/Col composites were found to be capable of overcoming bone loss, such as osteoporosis, by accelerating the formation of cancellous bone at the implantation site thereof. Specifically, the HAp/Col composites were found to be utilized in topical treatment of bone loss including osteoporosis as an excellent material for increasing bone mass that has been incorporated in the bone metabolism of the host, thereby accelerating bone formation.

All publications, patents, and patent applications cited herein are incorporated herein by reference in their entirety.

INDUSTRIAL APPLICABILITY

Composites having structures similar to those of natural bones and comprising calcium salt (particularly hydroxyapatite) and collagen of the present invention can regulate biodegradation rate while maintaining mechanical strength. Implantation of such composites in the body can effectively increase bone mass at desired sites. Thus, such composites can be utilized for treating, for example, osteoporosis.

What is claimed is:

1. A method for regulating the biodegradation rate of a composite biomaterial comprising hydroxyapatite and collagen by introducing crosslinking to collagen in said composite biomaterial, wherein the composite biomaterial has a microstructure in which the c-axis of hydroxyapatite is oriented along the collagen fibers.

2. The method according to claim 1, wherein the crosslinking is introduced in at least 1% of reactive functional groups in collagen.

3. The method according to claim 1, wherein the crosslinking is introduced by a reaction utilizing glutaraldehyde.

4. The method according to claim 3, wherein 10 μmol to 10 mmol of the glutaraldehyde is used per g of collagen in said composite biomaterial.

5. The method according to claim 1, wherein the crosslinking is introduced by using one or more crosslinking agent(s) selected from the group consisting of aldehyde crosslinking agents, isocyanate crosslinking agents, carbodiimide crosslinking agents, polyepoxy crosslinking agents, and transglutaminase.

6. The method according to claim 5, wherein the one or more crosslinking agent(s) is selected from the group consisting of glutaraldehyde, formaldehyde, hexamethylene diisocyanate, 1-ethyl-3-(3-dimethylaminopropyl) carbodiimide hydrochloride, ethylene glycol diglycidyl ether, and transglutaminase.

7. The method according to claim 1, wherein the crosslinking is introduced in at least 5% of reactive functional groups in collagen.

8. The method according to claim 1, wherein 50% or more of the crosslinked composite biomaterial remains after 4 weeks in a natural bone.

9. A method for preparing a composite biomaterial by introducing crosslinking to collagen in said composite biomaterial, wherein the composite biomaterial comprises hydroxyapatite and collagen and has a microstructure in which the c-axis of hydroxyapatite is oriented along the collagen fibers.

10. The method according to claim 9, wherein the crosslinking is introduced in at least 1% of reactive functional groups in collagen.

11. The method according to claim 9, wherein the crosslinking is introduced in at least 5% of reactive functional groups in collagen.

12. The method according to claim 9, wherein the crosslinking is introduced by using one or more crosslinking agent(s) selected from the group consisting of aldehyde crosslinking agents, isocyanate crosslinking agents, carbodiimide crosslinking agents, polyepoxy crosslinking agents, and transglutaminase.

13. The method according to claim 12, wherein the one or more crosslinking agent(s) is selected from the group consisting of glutaraldehyde, formaldehyde, hexamethylene diisocyanate, 1-ethyl-3-(3-dimethylaminopropyl) carbodiimide hydrochloride, ethylene glycol diglycidyl ether, and transglutaminase.

14. The method according to claim 9, wherein the crosslinking is introduced by a reaction utilizing glutaraldehyde.

15. The method according to claim 14, wherein 10 μmol to 10 mmol of the glutaraldehyde is used per g of collagen in said composite biomaterial.

16. The method according to claim 9, wherein 50% or more of the crosslinked composite biomaterial remains after 4 weeks in a natural bone.

* * * * *